(12) United States Patent
Pilchowski

(10) Patent No.: US 7,059,054 B2
(45) Date of Patent: Jun. 13, 2006

(54) CUTTING BLADES HAVING POINTED TIP, ULTRA-SHARP EDGES, AND ULTRA-FLAT FACES

(75) Inventor: Jörg Pilchowski, Bellevue, WA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/746,817

(22) Filed: Dec. 24, 2003

(65) Prior Publication Data

US 2005/0144789 A1 Jul. 7, 2005

(51) Int. Cl.
*B26B 9/00* (2006.01)
(52) U.S. Cl. .................. 30/350; 30/346.53; 606/167
(58) Field of Classification Search ............... 30/350, 30/346.53, 346.54; 76/104.1; 606/167
See application file for complete search history.

(56) References Cited

U.S. PATENT DOCUMENTS

| | | | |
|---|---|---|---|
| 5,317,938 A * | 6/1994 | de Juan et al. ........... 76/104.1 |
| 5,338,400 A | 8/1994 | Jerman |
| 5,579,583 A * | 12/1996 | Mehregany et al. ......... 30/342 |
| 5,842,387 A | 12/1998 | Marcus et al. |
| 6,099,543 A * | 8/2000 | Smith ..................... 606/167 |
| 6,615,496 B1* | 9/2003 | Fleming et al. ............ 30/350 |
| 2002/0078576 A1* | 6/2002 | Carr et al. ................. 30/357 |
| 2004/0143975 A1* | 7/2004 | Hamada et al. ......... 30/346.57 |
| 2004/0186493 A1* | 9/2004 | McWhorter et al. ....... 606/166 |

* cited by examiner

*Primary Examiner*—Hwei-Siu Payer
(74) *Attorney, Agent, or Firm*—Black Lowe & Graham PLLC

(57) ABSTRACT

An apparatus and method for a cutting blade having a pointed tip and ultra-flat faces that intersect at ultra-sharp edges. The cutting blade is batch-fabricated on a standard {100} semiconductor mono-crystalline silicon wafer using conventional anisotropic wet etching silicon micromachining techniques as a pair of spaced-apart substantially parallel and planar top and bottom surfaces each formed in {100} planes of a {100} mono-crystalline silicon substrate with first and second mutually rotated cutting edges formed between the top and bottom surfaces of the substrate and substantially parallel thereto in adjacent {111} planes that form a first pointed tip at an intersection therebetween, and having third and fourth cutting edges formed between the top and bottom surfaces of the substrate and substantially parallel thereto in adjacent {110} planes with the third and fourth cutting edges forming different pointed intersections with the first and second mutually rotated cutting edges.

20 Claims, 3 Drawing Sheets

CUTTING BLADES HAVING POINTED TIP, ULTRA-SHARP EDGES, AND ULTRA-FLAT FACES

FIELD OF THE INVENTION

The present invention relates to cutting blade devices and methods of forming the same, and in particular to cutting blades formed by microstructuring a substrate of mono-crystalline silicon.

BACKGROUND OF THE INVENTION

Small and ultra-sharp cutting blades with precise geometry control are needed in many fields, e.g. to perform precise surgical cuts in organic tissue and for micro-sample preparation. It is known in the art to form cutting blades by microstructuring a substrate of mono-crystalline silicon.

Currently, dimensions of silicon devices can be controlled accurately and repeatably. Silicon as a crystallographic material and its processing have been well characterized by the semiconductor industry. Crystal axes and planes in silicon are typically described in terms of Miller notation. FIG. 1 illustrates this notation on a cubic lattice with the three fundamental translation vectors $a_1$, $a_2$, and $a_3$, where $|a_1|=|a_2|=|a_3|$, and angles between $a_1$, $a_2$ and $a_2$, $a_3$ and $a_3$, $a_1$ are all 90 degrees. Some of the important planes are indicated, for example, the plane ABCD is designated (001), the plane ABE is designated (111), and the plane GHIK is designated (110). Planes with negative indices are also described using Miller notation. For example, the plane AED is defined by $(1,-1,1)$ and the plane CDF is defined by $(-1,-1,-1)$. If the lattice points are occupied by identical atoms, then the atom configurations in many of the Miller planes are the same. For example, the planes designated $(111)$, $(1,-1,1)$ and $(-1,-1,-1)$ all belong to the same family of $\{111\}$ planes.

Indices of lattice plane direction, i.e., of the line normal to the lattice plane, are simply the vector components of the direction resolved along the coordinate axes. Thus the (111) plane has a direction written as [111], and so on. Similar conventions are used to define directions relative to the other planes and families of planes.

The intersection line between planes is described by a vector. For example, in FIG. 1 the $(-1,1,1)$ plane CBE and the $(-1,1,1)$ plane CBF intersect along the line BC which is oriented in the $[-1,-1,0]$ direction. In terms of groups of planes and directions, the $\{111\}$ planes intersect $\{100\}$ planes along <110> directions. Simple vector calculations yield the intersection angles between planes. For example, the plane normal vectors $[-1,-1,1]$ and $[1,1,1]$ intersect at an angle of 109.47°.

It should be noted that (hkl) refers to any one of a series of parallel planes, and that [uvw] refers to any one of a series of parallel directions in a cubic crystal. This may be seen by a simple shifting of the origin for the references axes.

Mono-crystalline silicon has a diamond lattice wherein each lattice point is occupied with an identical silicon atom. Here, the $\{111\}$ planes are the closest spaced among the low-index planes with a separation of 3.135 Angstroms. Many fabrication processes are orientation-sensitive; that is, they depend on the direction in which the crystal slice is cut. Many mechanical and electronic properties of the crystal and its surface are orientation-dependent. Wafer manufacturers typically provide silicon wafers with flats to help identify crystal orientations. Silicon wafers with a $\{100\}$ surface are provided with a flat along a <110> direction. In this orientation, $\{111\}$ planes intersect the $\{100\}$ surface parallel and perpendicular to the wafer flat, at an angle of 54.74 degrees.

The atom density in the principal planes can be shown to be in the ratio $\{100\}:\{110\}:\{111\}=1:1.414:1.155$. Since atoms in these planes have 2, 1, and 1 dangling bonds respectively, the bond densities are in the ratio $1:0.707:0.577$. Crystal dissolution is related to the density of broken bonds; therefore it is slowest in the <111> directions, and will delineate the $\{111\}$ faces. Chemically selective etches will preferentially etch silicon by exposing $\{111\}$ planes.

Precise, three-dimensional structures are generally fabricated in an etchable substrate material, particularly in silicon, by anisotropic wet etching of the mono-crystalline silicon substrate. Anisotropic etches cause etching certain crystallographic planes of silicon much more rapidly than others by using some etchants such as mixtures of KOH and water or mixtures of ethylene diamine, pyrocatechol, and water. All of these etchants etch the $\{111\}$ silicon planes much more slowly than the other low order $\{100\}$ or $\{110\}$ planes.

Typical values for the relative etch rates for KOH etchants for the three planes of interest are $(111)=1$, $(100)=100$, and $(110)=170$ as discussed in H. Seidel et al, "Anisotropic Etching of Crystalline Silicon in Alkaline Solutions", J. Electrochem. Soc., Vol. 137, No. 11, November 1990, pages 3612–3626. These values vary, however, the etch rate ratios remain very large, and account for the tremendous anisotropy seen. It is possible to obtain very low-etched surface roughness for a "mirror-like" finish. For most micromachining and active circuit processing, e.g., MOS devices, silicon wafers with a $\{100\}$ surface are used.

Anisotropic or "orientation-dependent" etchants thus etch much faster in one direction than in another. KOH, for example, slows down markedly at the $\{111\}$ planes of silicon, relative to etch rates for other planes. In general, the slowest etching planes are exposed as the etch progresses. It is well-known that etching at "concave" or inside corners in $\{100\}$ silicon stops at intersecting $\{111\}$ planes. For example, if an opening in an etch mask forms a rectangle, an anisotropic etchant will etch down exposing $\{111\}$ planes to form a V-groove with respect to two opposing sides.

However, it is also well-known that "convex" or outside corners are undercut with respect to the etch mask, so that if a window in an etch mask is formed which is more complicated in shape than a rectangle, any convex protrusion will etch back to the "farthest" $\{111\}$ plane given enough time. As disclosed in U.S. Pat. No. 5,338,400, "MICROMACHINING PROCESS FOR MAKING PERFECT EXTERIOR CORNER IN AN ETCHABLE SUBSTRATE," the complete disclosure of which is incorporated herein by reference, a number of corner compensation techniques are known that limit or eliminate undercutting of convex corners.

SUMMARY OF THE INVENTION

A cutting blade that overcomes limitations of prior art cutting blades by microstructuring of a substrate of mono-crystalline silicon having spaced-apart top and bottom substantially parallel and planar $\{100\}$ surfaces to form a plurality of ultra-flat faces in $\{111\}$ and $\{110\}$ planes between the top and bottom substrate surfaces and to form a pointed tip between the top and bottom substrate surfaces by a common intersection of the plurality of faces.

According to another aspect of the invention, a first pair of the $\{111\}$ planes intersect at an angle of about 109.47 degrees to form a first cutting edge adjacent to the pointed tip along a <110> direction, and a second pair of the {111} planes intersect to form a second cutting edge adjacent to the pointed tip along another <110> direction, the first and second pairs of {111} planes forming an included angle therebetween of about 90 degrees at the cutting edges.

According to another aspect of the invention, the cutting blade of the invention includes two additional pairs of faces formed in {110} planes between the first and second substrate surfaces with a pair of cutting edges formed by common intersections along <100> directions of the respective pairs of faces formed in {110} planes. The planes in a pair of {110} planes intersect each other at an angle of about 90 degrees.

According to another aspect of the invention, the two pairs of faces formed in {110} planes each intersect one of the first and second pair of faces formed in {111} planes, whereby additional points are formed by common intersections of each of the two pairs of faces formed in {110} planes with the respective first and second pair of faces formed in {111} planes forming an included angle therebetween of 135 degrees at the cutting edges.

According to another aspect of the invention, the two pairs of faces formed in {110} planes and the first and second pair of faces formed in {111} planes are symmetrically positioned between the top and bottom substrate surfaces. Therefore, the cutting edges formed by the intersection of the {110} planes and the {111} planes are positioned equidistant from the top and bottom substrate surfaces providing an uninterrupted edge around the blade perimeter. However, according to still another aspect of the invention, the two pairs of faces formed in {110} planes and the first and second pair of faces formed in {111} planes are asymmetrically positioned between the top and bottom substrate surfaces, whereby the cutting edges formed by the intersection of the {110} planes and the {111} planes are off set toward either the top or the bottom substrate surface providing an uninterrupted edge around the blade perimeter.

According to yet another aspect of the invention, the two pairs of faces formed in {110} planes are elongated as compared with the first and second pair of faces formed in {111} planes, whereby the cutting blade is elongated.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF PREFERRED EMBODIMENT

In the Figures, like numerals indicate like elements.

The present invention is an apparatus and method for a cutting blade having a pointed tip and ultra-flat faces that intersect at ultra-sharp edges. Accordingly, the cutting blade of the invention is batch-fabricated on a standard semiconductor mono-crystalline silicon wafer with {100} top and bottom surfaces, using conventional anisotropic wet etching silicon micromachining techniques. A pair of spaced-apart substantially parallel and planar top and bottom surfaces each formed in {100} planes of a mono-crystalline silicon substrate with first and second mutually rotated cutting edges formed between the top and bottom surfaces of the substrate and substantially parallel thereto in adjacent {111} planes that form a first pointed tip at an intersection therebetween, and having third and fourth cutting edges formed between the top and bottom surfaces of the substrate and substantially parallel thereto in spaced-apart and substantially parallel {110} planes with the third and fourth cutting edges forming different pointed intersections with the first and second mutually rotated cutting edges.

According to one embodiment of the invention, the cutting edges are symmetrically positioned between the top and bottom surfaces of the substrate.

According to another embodiment of the invention, the cutting edges are asymmetrically positioned between the top and bottom surfaces of the substrate.

Figure 1:
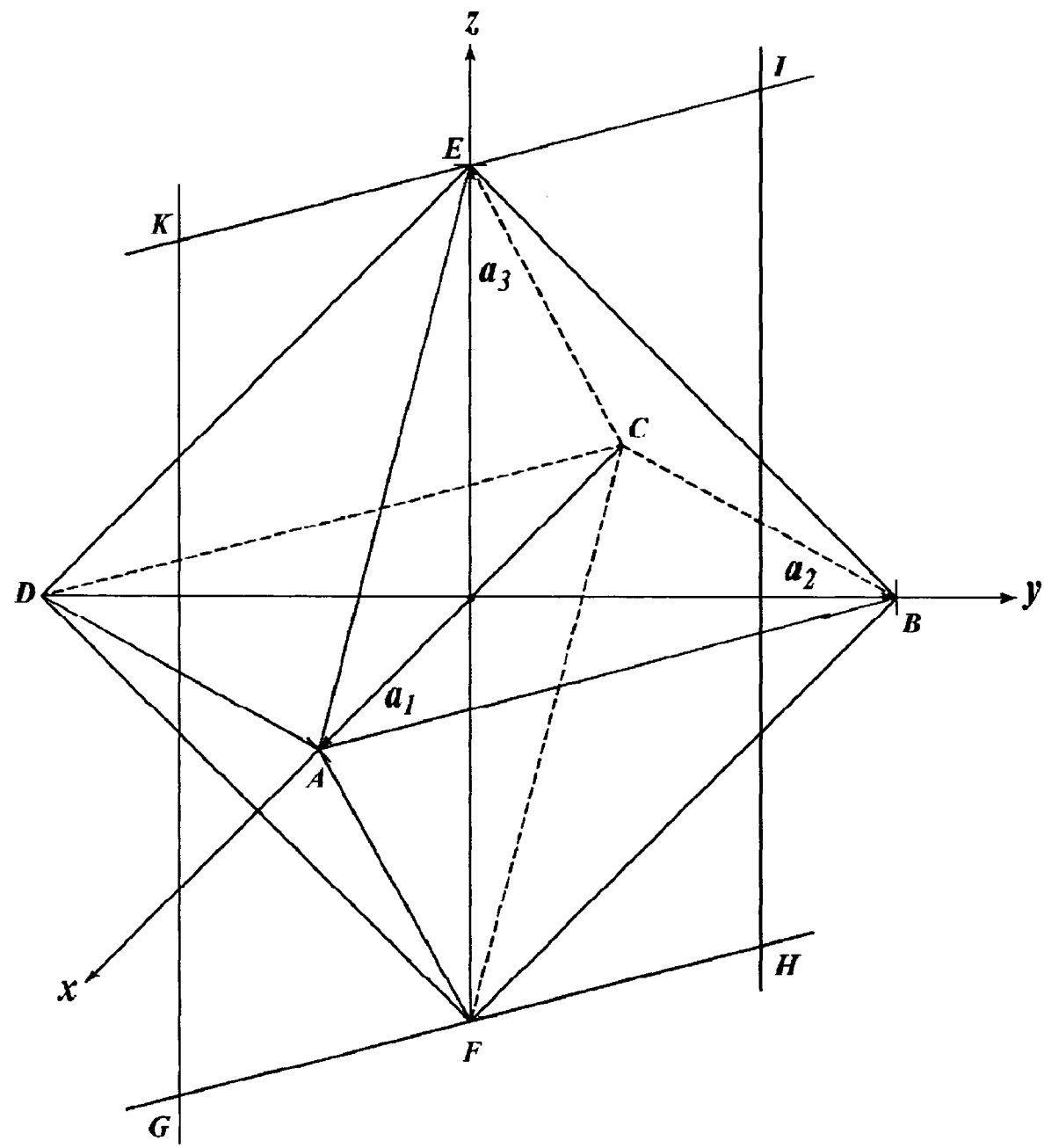
FIG. 1 illustrates planes of a cubic lattice.
Figure 2:
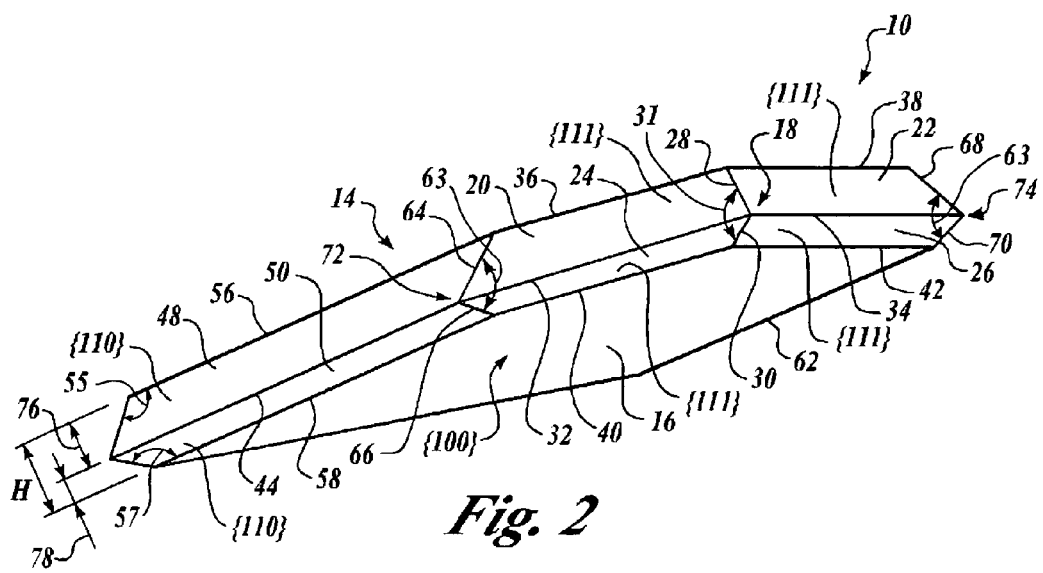
FIG. 2 is a perspective view of an exemplary embodiment of the cutting blade of the invention.
Figure 3:
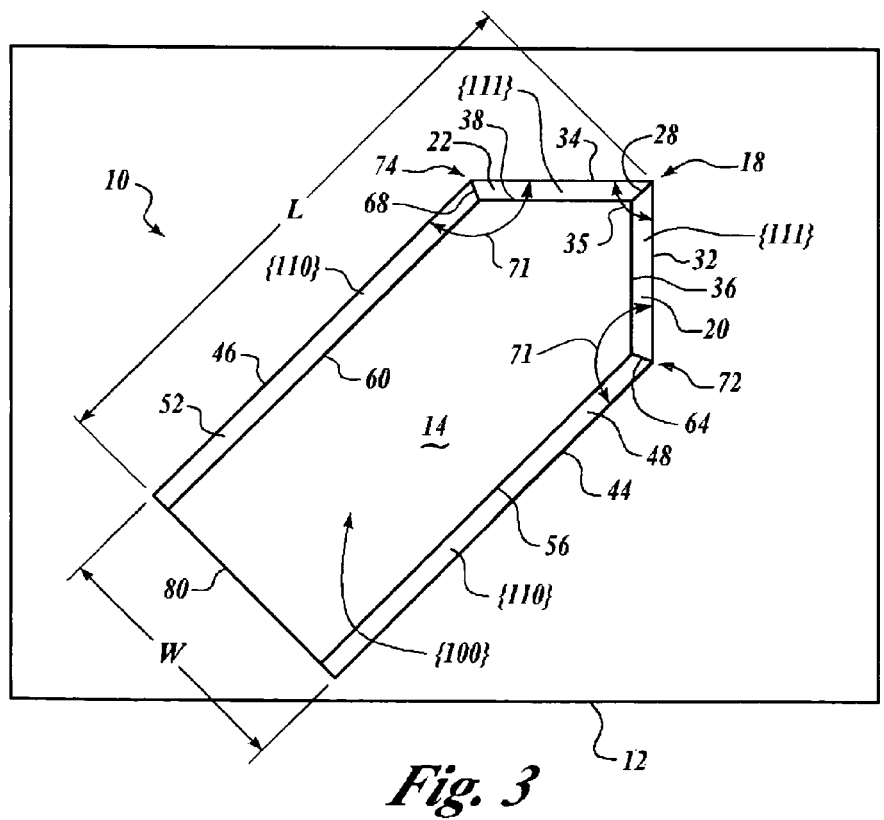
FIG. 3 is a top plan view of the exemplary embodiment of the cutting blade of the invention illustrated in FIG. 2.
Figure 4:
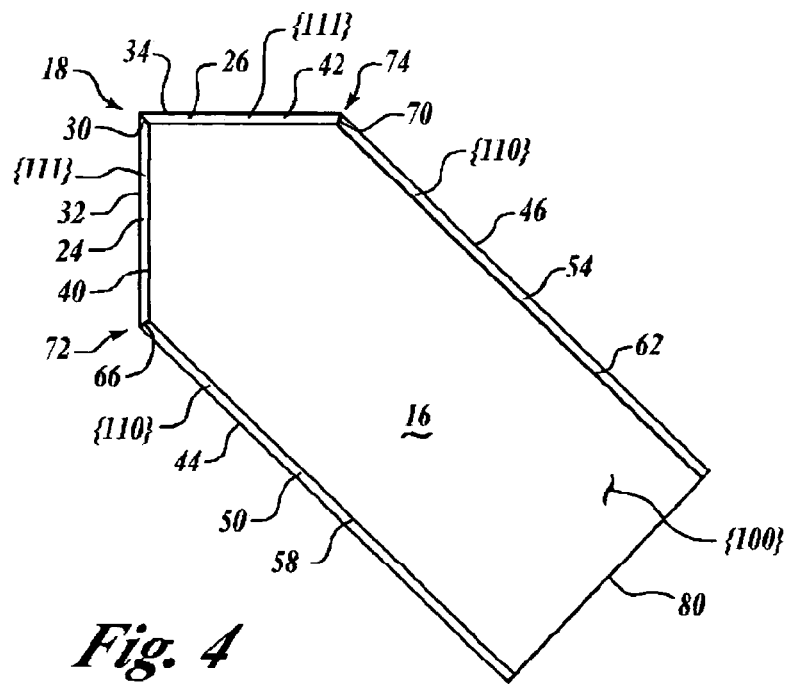
FIG. 4 is a bottom plan view of the exemplary embodiment of the cutting blade of the invention illustrated in FIG. 2.

FIGS. 2, 3 and 4 illustrate the cutting blade of the invention embodied as a cutting blade 10 formed in a standard semiconductor mono-crystalline silicon wafer 12 (shown by example in FIG. 3) by conventional silicon micromachining techniques such as anisotropic wet etching techniques that are well-known in the art for micromachining of silicon. The cutting blade 10 is, for example, formed in a wafer of {100} silicon having substantially planar top and bottom surfaces 14, 16 spaced apart by the thickness of the wafer 12, wherein "top" and "bottom" are used for convenience and clarity and are not intended to in any way limit the scope of the claimed invention. When the cutting blade 10 is formed in a wafer of {100} silicon, the top and bottom surfaces 14, 16 are of the family of {100} planes of the crystal structure, commonly referred to as crystallographic planes.

The cutting blade 10 is formed having a lead pointed tip 18 formed by a common intersection of ultra-flat blade tip faces 20, 22, 24, 26 that are all formed intermediate between the top and bottom surfaces 14, 16 in {111} planes. The {111} planes that form the ultra-flat blade tip faces 20, 22, 24, 26 are all produced with the 54.74 degree angles relative to the top and bottom surfaces 14, 16 when etched using an anisotropic etchant, such as KOH and water, as discussed above. The {111} planes 20, 24 intersect at an angle of 109.47 degree, and the {111} planes 22, 26 also intersect at an angle of 109.47 degree. The {111} planes 20, 22 intersect at an angle of 109.47 degree, and the {111} planes 24, 26 also intersect at an angle of 109.47 degree. According to the invention, the blade tip faces 20, 22, 24, 26 are etched to obtain very low-etched surface roughness for a "mirror-like" finish, as discussed above, whereby the blade tip faces 20, 22, 24, 26 are produced as the ultra-flat faces of the invention.

Because the blade tip faces 20, 22, 24, 26 are ultra-flat they intersect at ultra-sharp edges. The two top blade tip faces 20, 22 intersect at a first or top ultra-sharp blade tip edge 28, and the two bottom blade tip faces 24, 26 intersect at a second or bottom ultra-sharp blade tip edge 30. The blade tip edges 28 and 30 include a right angle 31. The ultra-flat top blade tip faces 20, 22 intersect the respective ultra-flat bottom blade tip faces 24, 26 at respective first and second co-planar ultra-sharp leading cutting blade tip edges 32, 34 that are substantially parallel with the blade's top and bottom surfaces 14, 16. The blade tip edges 32 and 34 include a right angle 35.

This is a significant improvement over prior art cutting blades formed by etching mono-crystalline silicon on single {111} planes through the entire thickness of the wafer. Such blades, by comparison to the cutting blades of the present invention, are "plow" shaped and tend to tear tissue. The cutting blade 10 of the invention, by contrast to prior art cutting blades, are ultra-sharp and capable of clean and precise surgical cuts in organic tissue because the tip 18 and ultra-sharp blade tip cutting edges 32, 34 are formed by intersections of different {111} planes intermediate ultra-sharp top surface edges 36, 38 and bottom surface edges 40, 42 formed respectively between the top blade tip faces 20, 22 and the wafer top surface 14, and between the bottom blade tip faces 24, 26 and the wafer bottom surface 16.

Additionally, co-planar spaced-apart and substantially parallel ultra-sharp blade side cutting edges 44, 46 (best shown in FIGS. 3 and 4) are formed of respective pairs of top and bottom blade side faces 48, 50 and 52, 54 all formed of {110} planes of the wafer 12. The pairs of top and bottom blade-side faces 48, 50 and 52, 54 therefore intersect the respective top and bottom surfaces 14, 16 at included angles 55 and 57 each of 45 degrees to form respective top and bottom surface edges 56, 58 and 60, 62. As a result, the blade side cutting edges 44, 46 are formed of included angles 63 of 90 degrees between intersecting pairs of {110} planes 48, 50 and 52, 54, respectively.

Furthermore, because the crystal planes {111} intersect the {110} planes at 144.74 degrees, the first pair of top and bottom blade side faces 48, 50 intersect the respective top and bottom blade tip faces 20, 24 at included angles of 144.74 degrees and thereby form ultra-sharp blade tip corner edges 64, 66 therebetween. Similarly, the second pair of top and bottom side blade faces 52, 54 intersect the respective tip top and bottom blade tip faces 22, 26 at included angles of 144.74 degrees and thereby form ultra-sharp blade tip corner edges 68, 70 therebetween. Ultra-sharp side pointed blade corner tips 72, 74, similar to the lead pointed tip 18, are formed with included angles 71 of 135 degrees at the respective intersections of the ultra-sharp blade corner cutting edges 64, 66 and 68, 70.

The ultra-sharp cutting blades 10 are thereby formed in the wafer 12 for performing precise surgical cuts in organic tissue and for preparing micro-samples. The cutting blades can be any width W, length L, and height H. For example, according to one embodiment of the invention, the blade length L is elongated as compared to the blade width W. According to another embodiment of the invention, the cutting blade 10 is formed having a width W of about 2.50 mm and a length L of about 6.25 mm. The height H of the cutting blade depends on the thickness of the {100} monocrystalline silicon wafer used; a typical value would be a height H of about 525 microns. Because the cutting blade 10 is much smaller than the wafer 12, as many as several hundred of the cutting blades 10 are batch-fabricated on one standard semiconductor mono-crystalline silicon wafer 12 by either the known silicon micromachining techniques described herein or another proprietary silicon etching techniques.

Micromachining of the wafer 12 to produce a plurality of the cutting blades 10 includes sequential surface masking, photolithographic patterning of mask and selective material removal in wet and dry etch chemistries. Anisotropic wet chemical etching of the mono-crystalline silicon wafer 12 exposes certain crystallographic planes that form the faces of the blade 10. Crystallographic planes form the blade tip faces 20, 22, 24, 26 and the blade respective blade side faces 48, 50 and 52, 54 of the blade, whereby very smooth, even mirror-like surfaces and ultra-sharp intersections are guaranteed.

The lead and corner point intersections 18, 72, 74 and lead and side line intersections 32, 34 and 44, 46 of the crystallographic planes are ultra-sharp. Blade heights 76, 78 above and below the cutting edges are controlled very accurately and are optionally formed asymmetric, i.e., at different heights, with the point and line intersections 18, 72, 74 and 32, 34 and 44, 46 all being co-planar at different distances from the top and bottom surfaces 14, 16, as illustrated by example and without limitation in FIGS. 2, 3, 4. Alternatively, the blade heights 76, 78 above and below the cutting edges are symmetric, i.e., the same height, with the co-planar point and line intersections 18, 72, 74 and 32, 34 and 44, 46 being equidistant from the top and bottom surfaces 14, 16, as illustrated by example and without limitation in FIG. 5.

The blade tip and side cutting edges 32, 34, 44, 46 form a continuous cutting edge that extends continuously around the entire length L and width W of the blade 10 except for a cut aft end 80. After batch fabricating several hundred of the blades 10 on a single silicon wafer 12, the blades 10 are separated by dicing and are ready for further assembly into a holding device determined as a function of desired application. The blade 10 is scalable from several tens of millimeters to a few microns without a loss in precision. Several hundred silicon blades 10 of the invention are fabricated from a single silicon wafer using conventional wet anisotropic etching techniques and either known or proprietary corner compensation techniques, whereby profitable economy of scale is achieved.

Figure 5:
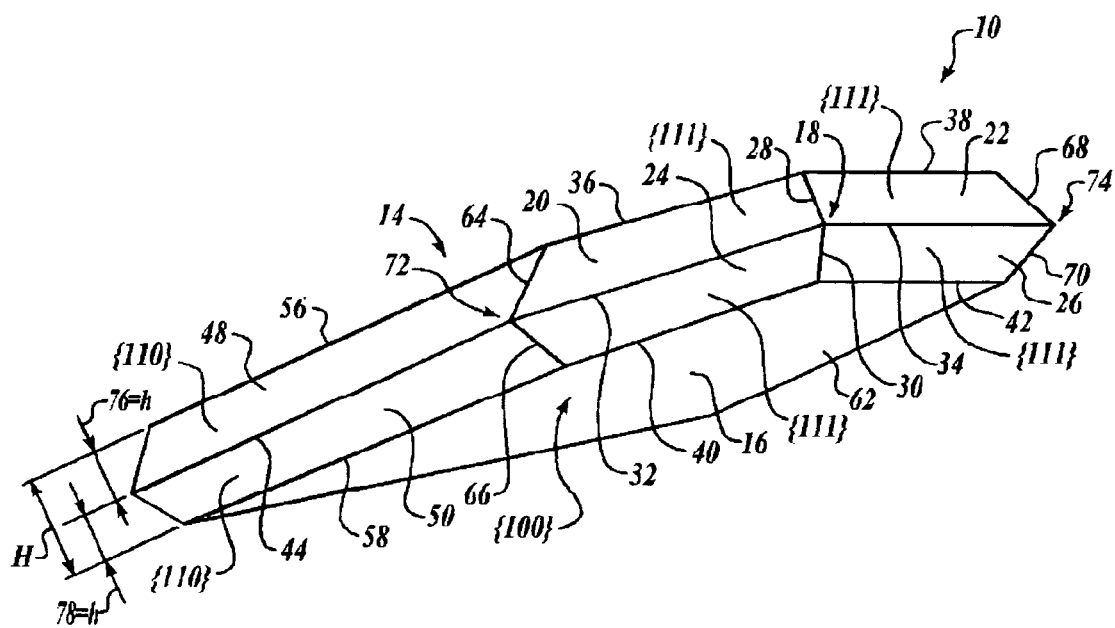
FIG. 5 is a perspective view of an exemplary embodiment of the cutting blade of the invention having symmetrically positioned cutting edges.

FIG. 5 illustrates by example and without limitation the cutting blade 10 being formed with blade heights 76, 78 above and below the cutting edges that are symmetric, i.e., the same height h, with the point and line intersections 18, 72, 74 and 32, 34 and 44, 46 being co-planar and equidistant from the top and bottom surfaces 14, 16.

While the preferred embodiment of the invention has been illustrated and described, it will be appreciated that various changes can be made therein without departing from the spirit and scope of the invention.

What is claimed is:

1. A cutting blade formed in {100} mono-crystalline silicon, the cutting blade comprising:
   a pair of spaced-apart substantially parallel and planar top and bottom surfaces each formed in {100} planes of a {100} mono-crystalline silicon substrate;
   first and second mutually rotated cutting edges formed between the top and bottom surfaces of the substrate and substantially parallel thereto in adjacent {111} planes and forming a first pointed tip at an intersection therebetween; and
   third and fourth cutting edges formed between the top and bottom surfaces of the substrate and substantially parallel thereto in adjacent {110} planes, the third and fourth cutting edges forming different pointed intersections with the first and second mutually rotated cutting edges.

2. The cutting blade of claim 1 wherein the cutting edges are symmetrically positioned between the top and bottom surfaces of the substrate.

3. The cutting blade of claim 1 wherein the cutting edges are asymmetrically positioned between the top and bottom surfaces of the substrate.

4. The cutting blade of claim 1 wherein the first and second cutting edges are mutually rotated at an included angle of about 90 degrees.

5. The cutting blade of claim 1 wherein the third and fourth cutting edges are elongated relative to the first and second cutting edges.

6. A cutting blade, comprising:
   a substrate of {100} mono-crystalline silicon having top and bottom surfaces formed in spaced-apart {100} planes;
   first and second cutting edges formed intermediate the top and bottom surfaces along respective common edges of respective first and second pairs of flat faces formed in {111} planes;
   a pointed tip formed between the top and bottom substrate surfaces by an intersection of the first and second pairs of flat faces; and
   one or more third cutting edges formed intermediate the top and bottom surfaces along respective common edges of one or more third pairs of flat faces formed in {110} planes.

7. The cutting blade of claim 6 wherein each of the one or more third cutting edges intersects one of the first and second cutting edges at a point formed intermediate the top and bottom surfaces.

8. The cutting blade of claim 7 wherein each of the first and second cutting edges and the one or more third cutting edges is offset relative to the top and bottom surfaces of the substrate.

9. The cutting blade of claim 8 wherein each of the first and second cutting edges and each of the one or more third cutting edges is substantially equidistant from the top and bottom surfaces of the substrate.

10. The cutting blade of claim 9 wherein the one or more third cutting edges are elongated relative to the first and second cutting edges.

11. A cutting blade, comprising:
    a substrate of mono-crystalline silicon having first and second substrate surfaces formed as spaced-apart first and second substantially planar surfaces formed in {100} planes;
    a plurality of faces formed in {111} and {100} planes between the first and second substrate surface; and
    a pointed tip formed between the first and second substrate surfaces by a common intersection of the plurality of faces.

12. The cutting blade of claim 11 wherein an intersection of a first air of the {111} planes forms a first cutting edge adjacent to the pointed tip.

13. The cutting blade of claim 12 wherein an intersection of a second pair of the {111} planes forms a second cutting edge adjacent to the pointed tip.

14. The cutting blade of claim 13 wherein the pointed tip further comprises inner right angle substantially perpendicular to the first and second substrate surfaces.

15. The cutting blade of claim 14 wherein the pointed tip further comprises an inner right angle substantially parallel to the first and second substrate surfaces.

16. The cutting blade of claim 11, further comprising:
    a pair of faces formed in {110} planes with an inner right angle between the first and second substrate surfaces; and
    a cutting edge formed between the first and second substrate surfaces by a common intersection of the pair of faces formed in {110}planes.

17. The cutting blade of claim 16 wherein a pair of faces formed in {110} planes intersect one of the faces formed in {111} planes.

18. The cutting blade of claim 16, further comprising;
    a pointed tip formed between the first and second substrate surfaces by a common intersection of a pair of faces formed in {110} planes and one of the faces formed in {111} planes; and
    wherein the pointed tip further comprises an inner angle of 135 degrees in a plane substantially parallel to the first and second planar surfaces of {100} planes.

19. The cutting blade of claim 18 wherein the faces formed in {110} planes and the faces formed in {111} planes are symmetric between the first and second substrate surfaces.

20. The cutting blade of claim 18 wherein the faces formed in {110} planes and the faces formed in {111} planes are asymmetric between the first and second substrate surfaces.

* * * * *